(12) United States Patent
Oesser

(10) Patent No.: US 8,778,422 B2
(45) Date of Patent: Jul. 15, 2014

(54) COMPOSITIONS FOR TREATING DEGENERATIVE JOINT DISEASES

(75) Inventor: Steffen Oesser, Glucksburg (DE)

(73) Assignee: Gelita AG, Eberbach (DE)

( * ) Notice: Subject to any disclaimer, the term of this patent is extended or adjusted under 35 U.S.C. 154(b) by 293 days.

(21) Appl. No.: 13/331,401

(22) Filed: Dec. 20, 2011

(65) Prior Publication Data

US 2012/0128737 A1    May 24, 2012

Related U.S. Application Data

(63) Continuation of application No. PCT/EP2010/058674, filed on Jun. 18, 2010.

(30) Foreign Application Priority Data

Jun. 22, 2009 (DE) .......... 10 2009 030 351

(51) Int. Cl.
*A61K 36/73* (2006.01)
*A61K 36/00* (2006.01)
*A61K 9/00* (2006.01)

(52) U.S. Cl.
USPC .......... 424/765; 424/725; 424/777; 424/778; 424/400

(58) Field of Classification Search
None
See application file for complete search history.

(56) References Cited

U.S. PATENT DOCUMENTS

| 4,804,745 | A | 2/1989 | Koepff et al. |
| 7,348,034 | B2 | 3/2008 | Murray et al. |
| 2006/0198810 | A1* | 9/2006 | Murray et al. ........... 424/74 |
| 2007/0154575 | A1* | 7/2007 | Shimoda et al. ........... 424/756 |
| 2011/0135721 | A1* | 6/2011 | Walbroel et al. ........... 424/456 |

FOREIGN PATENT DOCUMENTS

| EP | 0 254 289 B1 | 1/1988 |
| EP | 1 071 439 B1 | 1/2001 |
| JP | 2001238639 A * | 9/2001 |
| JP | 2004113141 A | 4/2004 |
| WO | WO 2008/003314 A1 | 1/2008 |
| WO | WO 2008/006589 A2 | 1/2008 |
| WO | WO 2008006582 A1 * | 1/2008 |
| WO | WO 2009/080778 A2 | 7/2009 |

OTHER PUBLICATIONS

Bello et al. (2008) Curr. Med. Res. Opin. vol. 22, No. 11, pp. 2221-2232.*
Chrubasik et al. (2006) Phytotherapy Research 20, pp. 1-3.*
Bello, A. et al., *Current Medical Research and Opinions*, 22 (11), pp. 2221-2232, (2008).
Deal, C. et al., *Osteoarthritis*, 25 (2), pp. 379-395 (1999).
*MMW Fortschritte der Medizin*, 145 (47), pp. 58-59, XP001525337 (2003).
Oszmianski J. et al., *Database Biotechabs/CA* (online), XP002490528, 11708 Abstract (1993).
Willich, S.N. et al., *Phytomedicine*, 17, pp. 87-93 (2010).
Winther, K. *International Cartilage Repair Society*, 16 (Supplement 1), pp. S8-S9 (2008).
Winther, K. *Abstracts of ICRS*, Abstract P18, (2007).
International Search Report PCT Application No. PCT/EP2010/058674, mailed Oct. 1, 2010.
Warholm et al., *Current Therapeutic Research*, (64), pp. 21-31 (2003).
Oesser et al., *Cell Tissue Research*, (311), pp. 393-399 (2003).
Product documentation, *Energy*, Issue No. 1 Rev., Annex No. 05—Skeletin, (Jan. 1, 2006), pp. 3-15.
Google search result for "Skeletin" for the period 2000-2007, printed Oct. 18, 2012.
Description of the product Atrevit, http://www.gorvita.com.pl/artrevit.html, printed Oct. 16, 2012.
Google search result "Atrevi" for the period 2000-2007, printed Oct. 18, 2012.

* cited by examiner

*Primary Examiner* — Chris R Tate
*Assistant Examiner* — Russell Fiebig
(74) *Attorney, Agent, or Firm* — Leydig, Voit & Mayer, Ltd.

(57) ABSTRACT

In order to provide a composition for the treatment of degenerative joint diseases with an improved efficacy, it is proposed that the composition comprises collagen hydrolysate and rosehip powder and/or extract, wherein the weight ratio of collagen hydrolysate to rosehip powder and/or extract, in each case in relation to dry mass, lies in the range of approximately 2:1 to approximately 100:1.

16 Claims, 6 Drawing Sheets

COMPOSITIONS FOR TREATING DEGENERATIVE JOINT DISEASES

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 777 bytes ASCII (Text) file named "709525ReplacementSequenceListing.txt," created Jan. 25, 2012.

The present invention relates to a composition, in particular in the form of a medication or a food supplement, for the treatment of degenerative joint diseases.

Degenerative joint diseases, which are characterised by wear or damage of the cartilage of the joint, are generally grouped together under the term arthrosis. The term osteoarthritis adopted from English language literature is sometimes also used synonymously. Degenerative joint diseases are widespread over the entire population, wherein the frequency of occurrence increases steeply with age. The joints most frequently affected are the knee and hip joints.

The causes of joint wear are varied and can lie both in a biological inferior quality of the cartilage tissue (primary arthrosis) and also in influencing factors such as mechanical overload (e.g. as a result of joint misalignment), inflammation or metabolic disorders (secondary arthrosis). In each case with advancing disease a complete loss of the joint cartilage can occur so that the subchondral bone surfaces are exposed and rub against one another, which causes considerable discomfort to the affected patients.

Cartilage tissue is predominantly composed of an extracellular matrix, the components of which are synthesised by the chondrocytes (cartilage cells) distributed in the matrix. In the case of joint cartilage (hyaline cartilage) the dry mass of the extracellular matrix comprises approximately 60% by weight of collagen (predominantly of type II), approximately 25 to 35% by weight of proteoglycans and also 15 to 20% by weight of non-collagenous proteins. The formation and degeneration of the extracellular matrix follow a complex regulatory mechanism, wherein in healthy cartilage tissue the chondrocytes react to a changed composition of the matrix by regulating the biosynthesis of the matrix components accordingly. The supply of the cartilage tissue with nutrients in this case only occurs as a result of the periodic pressure changes within the joint, since there are no blood or lymph vessels present in the cartilage.

It has long been known to treat degenerative joint diseases by oral administration of collagen hydrolysate. In the meantime, a series of clinical studies have been conducted on the efficacy of this treatment with respect to relieving the symptoms (see A. Bello and S. Oesser (2006), *Current Medical Research and Opinion* (22) 2221-2232). Although the exact mode of action of collagen hydrolysate has not yet been clarified, it is assumed that the collagen fragments are absorbed into the bloodstream and stimulate the synthesis of the extracellular matrix in the cartilage tissue by intervening in the above-described regulatory mechanism. It has been possible to prove by means of in vitro tests with chondrocytes that the biosynthesis and secretion of collagen is increased in the presence of collage hydrolysate (see S. Oesser and J. Seifert (2003), *Cell Tissue Research* (311) 393-399).

The object forming the basis of the invention is to provide a composition for the treatment of degenerative joint diseases with an improved efficacy.

This object is achieved according to the invention by a composition comprising collagen hydrolysate and rosehip powder and/or extract, wherein the weight ratio of collagen hydrolysate to rosehip powder and/or extract, in each case in relation to dry mass, lies in the range of approximately 2:1 to approximately 100:1.

It has surprisingly been found that the stimulating effect of collagen hydrolysate on the biosynthesis of collage and proteoglycans in the chondrocytes can be increased by a combination of rosehip powder or extract. This action is based on a synergistic effect, since no such stimulation is observed as a result of rosehip powder or extract alone.

The medicinal application of rosehips, even in association with arthrosis, is known per se. However, this application is based on an anti-inflammatory effect of a galactolipid (GOPO) contained in rosehip powder in particular. Inflammation can be the cause and/or accompanying symptom of degenerative joint diseases, and there are studies that show pain relief as a result of taking rosehip powder (see D. Warholm et al. (2003), *Current Therapeutic Research* (64) 21-31). However, an effect of rosehip powder or extract on the biosynthesis of cartilage constituents has not been described hitherto.

In the composition according to the invention the weight ratio of collagen hydrolysate to rosehip powder and/or extract, in each case in relation to dry mass, lies in the range of approximately 2:1 to approximately 100:1. The above-described synergistic effect is generally not detectable with weight ratios above approximately 100:1, i.e. with the use of less than approximately 1% by weight of rosehip powder and/or extract in relation to collagen hydrolysate. On the other hand, only an insignificant increase or no increase at all in this effect can be obtained by using more than approximately 50% by weight of rosehip powder and/or extract in relation to collagen hydrolysate (i.e. with a ratio of less than approximately 2:1). The weight ratio of collagen hydrolysate to rosehip powder and/or extract preferably lies in the range of approximately 5:1 to approximately 50:1, more preferred in the range of approximately 10:1 to approximately 20:1. Therefore, the described effect can be achieved with a limited quantity of rosehip powder and/or extract.

Within the framework of the present invention collagen hydrolysate is understood to be any hydrolysis product of collagen, which because of a sufficiently low molecular weight no longer gels under the conditions of the standard Bloom test, i.e. has a gel strength of 0 g Bloom. The collagen hydrolysate is preferably obtained by enzymatic hydrolysis of type I and/or type II collagen. It has been shown that the stimulating effect on the biosynthesis of the extracellular matrix of the cartilage tissue (which is composed predominantly of type II collagen) is substantially independent of the type of collage hydrolysate, and this indicates that the peptide fragments in collage hydrolysate of type I and type II have the same or a similar structure.

Suitable starting material for the production of collagen hydrolysate is in particular bone, skin, connective tissue (respectively type I) or cartilage (type II) from different animals. Typical starting materials are e.g. cattle bones, bovine split hide and pork rind, however, collagen hydrolysate can also be obtained e.g. from collagen from poultry or fish. In connection therewith, the production process for the collagen hydrolysate can be based both on native collagen and on gelatin, i.e. extracted and denatured collagen.

The collagen hydrolysate in the composition according to the invention preferably has an average molecular weight of approximately 0.3 kDa to approximately 30 kDa, in particular approximately 2 kDa to approximately 10 kDa. The molecular weight distribution of the collagen hydrolysate can be controlled by selecting suitable proteolytic enzymes (generally bacterial proteases). In addition, individual molecular weight fractions of the hydrolysate can be separated by ultrafiltration where appropriate processes, where appropriate.

In the broadest sense, the rosehip powder and/or extract in the composition according to the invention can relate to all products obtained from rosehips. Rosehips are the spurious fruits of different types of roses, wherein the rosehip of the dog rose (*Rosa canina*) is preferably used. They consist substantially of the fruit flesh and/or the pod (*Fructus cynosbati*) and the seeds (*Semen cynosbati*), these being nuts in the botanical sense. The fruit flesh without the nuts is also referred to as *Cynosbati sine semine*.

According to an embodiment of the invention, the composition comprises a rosehip powder composed of *Fructus cynosbati* and/or *Semen cynosbati*. In connection therewith, within the framework of the invention a powder is understood to be any substantially homogeneous product that contains all constituents of rosehips or the used parts of rosehips irrespective of the particle size. However, a powder with particles as fine as possible is preferred, since with this a homogeneous mixture with the collagen hydrolysate and, if necessary, further components of the composition according to the invention can be obtained more easily and the active constituents of the rosehip can go into solution more quickly. In particular, a rosehip powder can be obtained by drying and milling *Fructus cynosbati*, as is described in EP 1 071 439 B1, for example.

According to a further embodiment of the invention, the composition comprises a rosehip extract composed of *Fructus cynosbati* and/or *Semen cynosbati*. In connection therewith, within the framework of the invention an extract is understood to be any product that is obtained by the extraction of rosehips or the used parts of rosehips with a fluid extracting agent. The above-defined weight ratio of the rosehip extract to the collagen hydrolysate relates in this case to the dry substance of the extracted components without the extracting agent. The use of an extract is preferred over the use of a powder, since the composition of an extract can generally be reproduced more readily. Moreover, a rosehip extract can also be used directly in liquid form as component of a liquid composition according to the invention, which is not possible in the case of a rosehip powder. If a dried extract is used, then this can be dispersed or dissolved more readily than a rosehip powder.

It is particularly favourable if the rosehip extract is obtained by the extraction of *Fructus cynosbati* with an aqueous extracting agent containing up to 50% by vol. of ethanol. In particular, a purely aqueous extracting agent without ethanol can also be used, so that the rosehip extract obtained is completely and readily water-soluble. Interestingly, it has been shown that such aqueous or aqueous/alcoholic rosehip extracts, which are extremely effective within the framework of the present invention, frequently do not contain any detectable amounts of the galactolipid GOPO, which are considered responsible for the anti-inflammatory effect of known rosehip preparations. This indicates that the found synergistic effect, i.e. the increase in the effect of collagen hydrolysate on the biosynthesis of matrix components, is attributable to other hitherto unidentified constituents or components of the rosehip.

The rosehip extract can be subjected to different after-treatments before use in the composition according to the invention. Such an after-treatment preferably comprises an enzyme treatment and/or membrane filtration. Unwanted components of the extract can be reduced or removed by means of these processes, as a result of which the efficacy of the extract may be increased under some circumstances.

The enzyme treatment preferably comprises a treatment of the rosehip extract with one or more enzymes selected from glycosidases, cellulases and pectinases. Such enzyme mixtures are also used, inter alia, in the clarification of wine and are obtainable e.g. under the brand name Ultrazym®.

The membrane filtration preferably comprises a filtration of the rosehip extract with an exclusion size of approximately 1 kDa to approximately 500 kDa, in particular approximately 10 kDa to approximately 300 kDa. In this connection, substances with a molecular weight above the respective exclusion size are separated and the permeate is subsequently used for the composition according to the invention.

The present invention additionally relates to a medication or food supplement, which comprises the above-described composition comprising collagen hydrolysate and rosehip powder and/or extract. In particular, the invention relates to such a medication or food supplement for the treatment or prevention of degenerative joint diseases.

Since the essential constituents of the composition according to the invention are of animal or plant origin, no approval as medication is necessary and the composition can therefore also be declared and supplied as a food supplement, as has long been customary in the case of collagen hydrolysate. Harmful side-effects of the composition according to the invention are not indicated according to the current level of knowledge.

The degenerative joint diseases that can be treated with the medication or food supplement according to the invention comprise in particular arthrosis in all manifestations and generally all diseases associated with damage or wear of cartilage tissue, in particular rheumatoid arthritis, rheumatic-type diseases, spondylitis and fibromyalgia.

Because of its mode of action, the medication or food supplement according to the invention is not only suitable for the treatment of acute diseases, but also for the prevention thereof, in particular in the case of persons who are particularly at risk because of a metabolic disturbance or above-average strain on the joints (e.g. athletes): From this viewpoint, the invention also relates to a medication or food supplement of the above-described type for stimulating the formation of cartilage tissue.

The medication or food supplement can be in the form of a solution, a syrup, a powder or a granulate. When a rosehip powder is used in the composition according to the invention this is present in solid form overall, whereas when a rosehip extract is used, both a liquid and a solid composition can be formulated as medication or food supplement. The specified forms of administration allow an individual dosage by the user, alternatively a solution in pre-metered dose ampoules, for example, can also be supplied.

Alternatively, the medication or food supplement can also be provided in fixed pre-metered dose form, i.e. in particular in the form of tablets, film tablets, capsules, lozenges or sugar-coated pills. Advantageously, a dose of the medication or the food supplement comprises approximately 0.1 g to approximately 20 g of collagen hydrolysate, in particular approximately 1 g to approximately 10 g, which corresponds to a preferred daily dose. For example, a dose can comprise 10 g of collagen hydrolysate and consequently approximately 0.1 g to approximately 5 g of rosehip powder and/or extract.

These and further advantages of the invention are explained in more detail on the basis of the following examples with reference to the figures.

Figure 1:
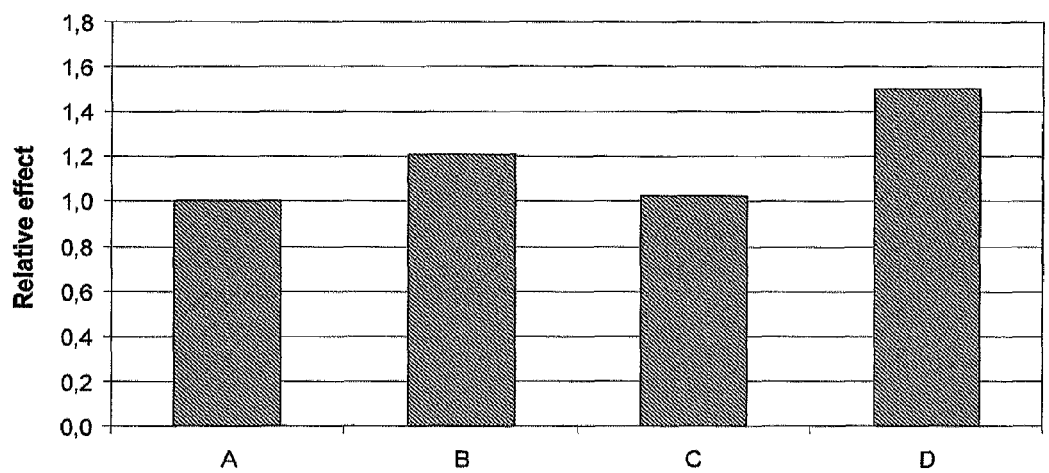
FIG. 1 is a graph relating to the biosynthesis of collagen (rosehip extract)

The synergistic effect of the composition according to the invention on the biosynthesis of the essential matrix components of cartilage tissue was established using an in vitro model with porcine and human chondrocytes.

Collagen Hydrolysate

The collagen hydrolysate used for the tests has an average molecular weight of approximately 3 kDa and is produced by hydrolysis of type I animal collagen by means of bacterial proteases. This collagen hydrolysate is supplied by the applicant under the name Fortigel® as a food supplement for stimulating the formation of cartilage tissue.

Rosehip Extract

An aqueous extract of rosehip pods (*Fructus cynosbati*) of the dog rose was used. Such a rosehip extract can be produced by extracting 1 kg of rosehip pods twice with 6 l water in each case at 50° C. for a period of 6 h. After being allowed to settle the extract solutions are combined and then clarified. After removal of the extracting agent, the extract can be dried in a vacuum at 50° C.

The dry mass of the rosehip extract obtained in this way corresponds to a yield in the range of approximately 35 to 45%. The extract does not contain any detectable amounts of the galactolipid GOPO.

Rosehip Powder

A rosehip powder produced according to a standardised process and distributed by Queisser Pharma GmbH & Co. KG (Flensburg) under the name LITOZIN® was used. This rosehip powder contains relatively high amounts of the galactolipid GOPO.

Cultivation of the Chondrocytes In Vitro

For the cell cultures porcine or human chondrocytes were isolated from cartilage tissue in the known manner and seeded on culture plates with a density of approximately 350 000 cells/cm2. Ham's F12 medium was used as culture medium with 10% foetal calf serum, 10 μm/ml of gentamicin and 5 μm/ml of amphotericin B. The cultivation occurred at 37° C. in an oxygen-reduced atmosphere (5% O2, 5% CO2 and 90% N2).

Collagen hydrolysate and/or rosehip extract were added to the culture medium according to the batch (see below).

Determination of the Collagen Biosynthesis

The quantification of the (substantially type II) collagen synthesised by the chondrocytes is achieved by radioactive marking with 14C proline which is incorporated into the collagen.

Radioactive 14C proline is firstly added to the culture medium and the chondrocytes are cultivated in these conditions up to the time of determination. To be able to distinguish the incorporated from the non-incorporated 14C proline during detection, the culture medium containing isotope is then replaced by pure culture medium for a period of 3 days. The culture medium is then discarded and the adherent cell layer is mixed with distilled water in order to destroy the cell membranes by osmotic stress and release cytosolic, non-bonded 14C proline. The cell debris with the synthesised extracellular matrix is pelletised by centrifugation. The pellet is re-suspended in fresh distilled water and mixed with a xylene scintillation cocktail. The amount of synthesised collagen can then be quantified by detection of the 14C proline with a beta counter.

Determination of the Proteoglycan Biosynthesis

The quantification of the proteoglycans synthesised by the chondrocytes is achieved by means of an alcian blue stain and photometric determination of the glycosamoglycans (GAG), which are constituents of the proteoglycans.

In order to determine the GAG content in the cell culture, the culture medium is firstly discarded and the adherent cell layer is rinsed with PBS buffer (pH 7). The cells are then fixed in a 10% formaldehyde solution in PBS for 2 hours at 4° C. After removal of the formaldehyde the alcian blue staining reagent (5% alcian blue in 3% acetic acid) is poured onto the cell layer and incubated overnight at 4° C. Non-bonded alcian blue is discarded and washed out by careful rinsing three to four times with PBS. The GAG complexes are dissolved out of the cell layer by adding acid guanidine solution (8 mol/l). The amount of glycosaminoglycans can then be quantified photometrically at a wavelength of 620 nm.

Determination of the RNA Expression of Collagen and Aggrecan

The amount of expressed RNA, which encodes type II collagen or aggrecan, an important proteoglycan, also serves as direct indicator for the biosynthesis of collagen and proteoglycans. The determination is conducted semi-quantitatively in relation to the RNA of glyceraldehyde-3-phosphate dehydrogenase (GAPDH).

The culture medium is firstly removed and dissolved by adding Trizol® to the cell layer. The RNA is isolated in a known manner with chloroform and isopropanol. The amount of isolated RNA is determined photometrically at 260 nm and 1 μg of RNA is then transcribed into cDNA by reverse transcription. The specific sequences are respectively amplified with the following primer pairs (for porcine chondrocytes):

```
Type II collagen:
                                    (SEQ ID No. 1)
5'-CCACTGCTCTCTGCCATACA-3'
                                    (SEQ ID No. 2)
5'-GTCCAGGTAGGCAATGCTGT-3'

Aggrecan:
                                    (SEQ ID No. 3)
5'-GGAGAAGAGATGCCAACAGC-3'
                                    (SEQ ID No. 4)
5'-ATGCTGCTCAGGTGTGACTG-3'

GAPDH:
                                    (SEQ ID No. 5)
5'-GGGCATGAACCATGAGAAGT-3'
                                    (SEQ ID No. 6)
5'-AAGCAGGGATGATGTTCTGG-3'
```

The amplification is conducted for each sample with 1 μl of cDNA, 19.65 μl of distilled water, 3 μl of 10× gold buffer, 2.4 μl of 25 mM $MgCl_2$, 0.6 mM of dNTP, 0.6 μl in each case of the specific primer and 0.15 μl of AmpliTaq® polymerase. The thermocycler program comprises initialisation at 95° C.

for 10 mM, denaturing at 94° C. for 1 mM, the addition of the primers at 69° C. (aggrecan), 64° C. (type II collagen) or 58° C. (GAPDH) for 30 and elongation at 72° C. for 30 s. There are conducted 35 cycles in each case before the polymerase is inactivated at 70° C. for 10 min. The cDNA products are then separated by electrophoresis on a 5% agarose-ethidium bromide gel and the amount thereof determined by densitometry with an imaging process. The expression of the collagen and aggrecan RNA is evaluated semi-quantitatively in relation to the GAPDH RNA.

Results with Rosehip Extract

The biosynthesis of collagen and of proteoglycans as well as the expression of collagen RNA and aggrecan RNA were determined for the following batches of cell cultures and respectively compared with one another:

Batch A: control (culture medium without collagen hydrolysate or rosehip extract)
Batch B: culture medium with 0.5 mg/ml of collagen hydrolysate
Batch C: culture medium with 0.035 mg/ml of rosehip extract (dry substance)
Batch D: culture medium with 0.5 mg/ml of collagen hydrolysate and 0.035 mg/ml of rosehip extract (dry substance)

For the determination of the biosynthesis of collagen and proteoglycans the cells were respectively cultivated for 3 days under the appropriate conditions, and respectively for 1 day for analysis of the RNA expression. Comparable results were respectively obtained with porcine and human chondrocytes.

The results for the biosynthesis of collagen, i.e. for batches B, C and D respectively in relation to batch A (control=1), are shown in graph form in FIG. 1. The results show the mean values from at least seven respective independent analyses.

While the biosynthesis of collagen is increased by approximately 20% by the addition of collagen hydrolysate, the addition of rosehip extract alone does not lead to any relevant effect. With the simultaneous addition of collagen hydrolysate and rosehip extract (in a weight ratio of approximately 14:1), however, an increase in the collagen biosynthesis by approximately 50% in relation to the control is observed. This result makes it clear that rosehip extract increases the stimulating effect of collage hydrolysate on the collagen biosynthesis in the form of a synergistic effect.

Figure 2:
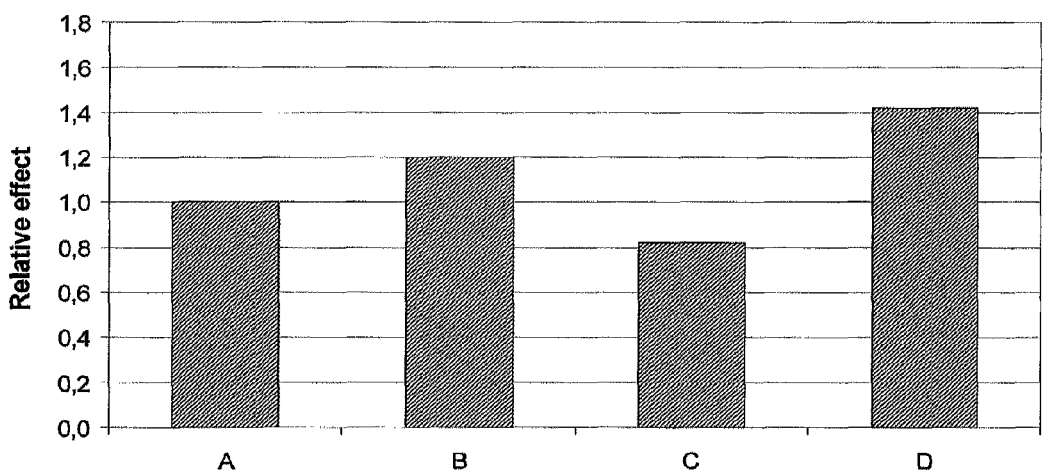
FIG. 2 is a graph relating to the biosynthesis of proteoglycans (rosehip extract)

The corresponding values for the biosynthesis of proteoglycans are shown in FIG. 2, wherein these are the mean values from at least six respective independent analyses. While in the case of batch C (rosehip extract alone) the proteoglycan biosynthesis observed here is even slightly lower than with the control, the rates of increase in the case of batches B (collagen hydrolysate) and D (collagen hydrolysate with rosehip extract) are comparable with those of the collagen biosynthesis.

Figure 3:
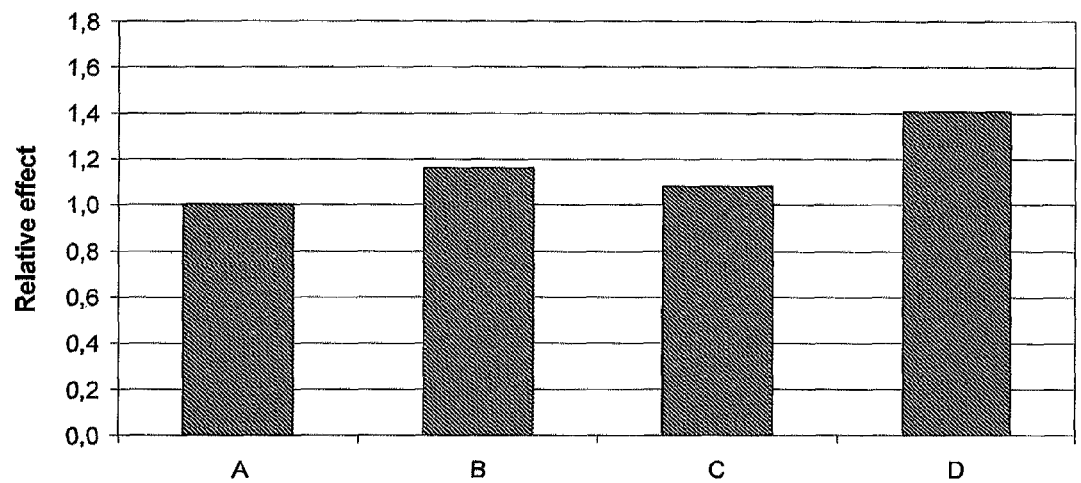
FIG. 3 is a graph relating to the expression of collagen RNA (rosehip extract)
Figure 4:
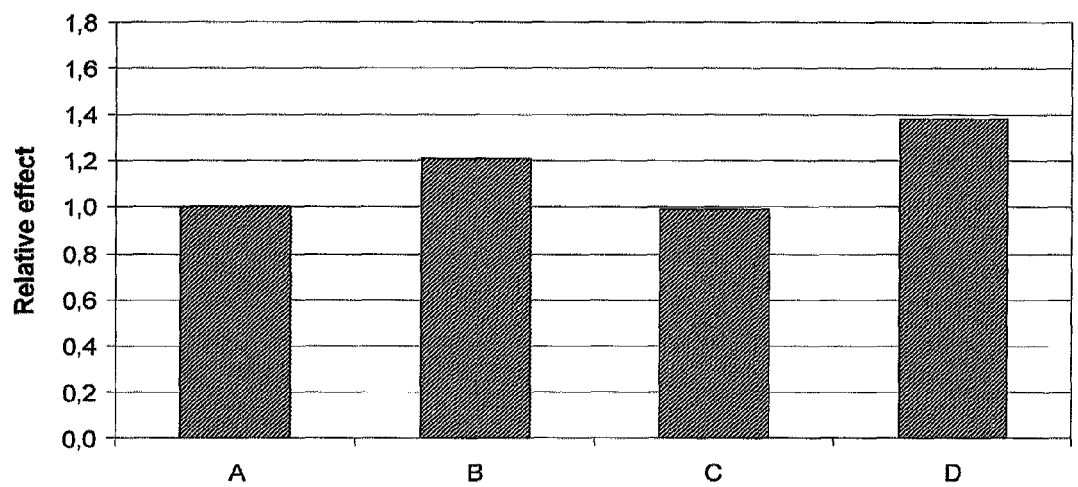
FIG. 4 is a graph relating to the expression of aggrecan RNA (rosehip extract)

This effect could also be confirmed with respect to the expression of RNA. FIG. 3 shows the results for the expression of collagen RNA (mean values respectively from 16 analyses) and FIG. 4 shows the results for the expression of aggrecan RNA (mean values respectively from ten analyses). In both cases the amount of RNA increased by approximately 20% in relation to the control as a result of the addition of collagen hydrolysate, and by approximately 40% as a result of the addition of collagen hydrolysate and rosehip extract in the weight ratio of approximately 14:1.

Figure 5:
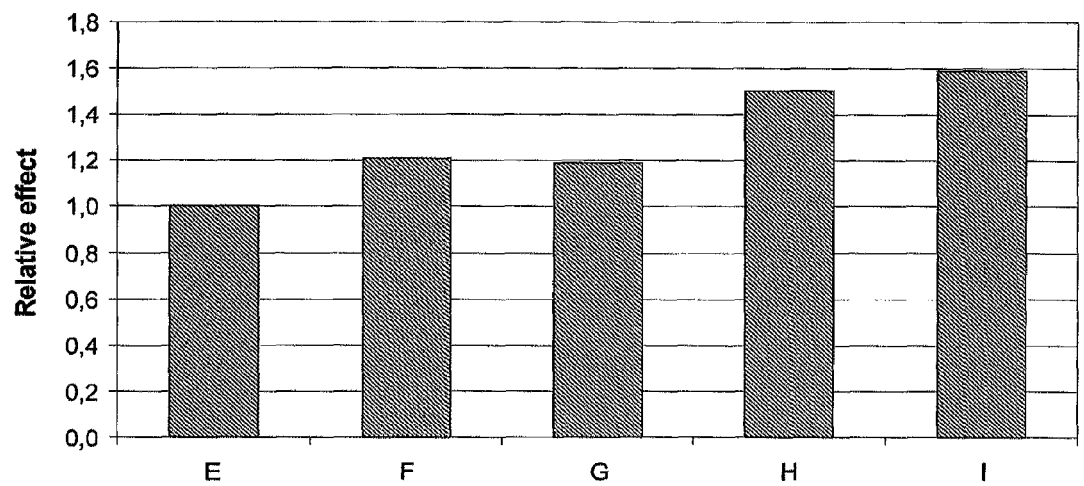
FIG. 5 is a graph relating to the biosynthesis of collagen (rosehip extract)
Figure 6:
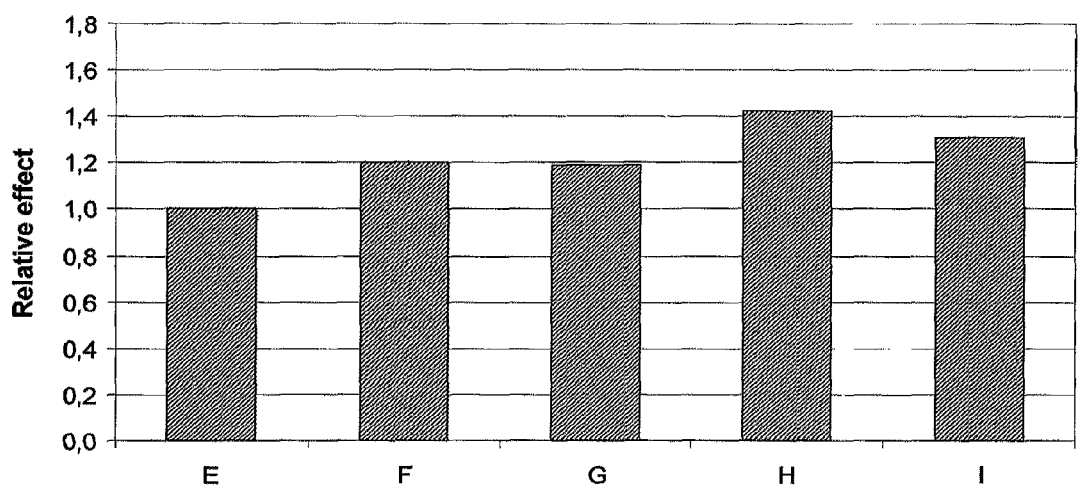
FIG. 6 is a graph relating to the biosynthesis of proteoglycans (rosehip extract)

Further tests were conducted to determine the effect of the amount of rosehip extract used. The following batches of cell cultures were compared with one another for this:

Batch E: control (without collagen hydrolysate or rosehip extract)
Batch F: 0.5 mg/ml of collagen hydrolysate
Batch G: 0.5 mg/ml of collagen hydrolysate and 0.0035 mg/ml of rosehip extract
Batch H: 0.5 mg/ml of collagen hydrolysate and 0.035 mg/ml of rosehip extract
Batch I: 0.5 mg/ml of collagen hydrolysate and 0.35 mg/ml of rosehip extract FIG. 5 shows the results with respect to the biosynthesis of collagen and FIG. 6 with respect to the biosynthesis of proteoglycans (mean values respectively from at least six independent analyses). In both cases, batch G (weight ratio of collagen hydrolysate to rosehip extract of approximately 140:1) merely demonstrates the same stimulating effect of approximately 20% as batch F (only collagen hydrolysate). Batch H (weight ratio of approximately 14:1) shows the respective increases of approximately 50% and approximately 40% corresponding to batch D above. If the amount of rosehip extract is multiplied by ten again (batch I, weight ratio of approximately 1.4:1), then in the case of the collagen biosynthesis only a disproportionately low increase to barely 60% results in relation to the control, and in the case of the proteoglycan biosynthesis the result is even poorer than with batch H.

Results with Rosehip Powder

The biosynthesis of collagen and proteoglycans as well as the expression of collagen RNA and aggrecan RNA were determined for the following batches of cell cultures and respectively compared with one another:

Batch K: control (culture medium without collagen hydrolysate or rosehip powder)
Batch L: culture medium with 0.5 mg/ml of collagen hydrolysate
Batch M: culture medium with 0.05 mg/ml of collagen hydrolysate
Batch N: culture medium with 0.5 mg/ml of collagen hydrolysate and 0.5 mg/ml of rosehip powder The cultivation of the cells and the subsequent analysis of the biosynthesis of collagen and proteoglycans as well as the RNA expression was respectively conducted as with the use of rosehip extract (see above).

The results for porcine chondrocytes described below are also substantially comparable with those that were observed with the use of rosehip extract. Similar results were obtained with human chondrocytes.

Figure 7:
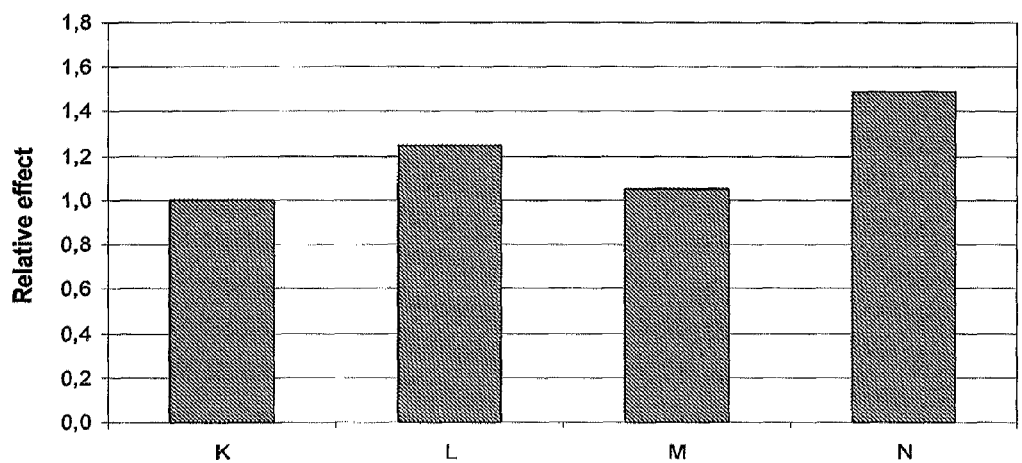
FIG. 7 is a graph relating to the biosynthesis of collagen (rosehip powder)

The results for the biosynthesis of collagen, i.e. for batches L, M and N in relation to batch K (control=1), are shown in FIG. 7. The results show the mean values from at least seven respective independent analyses. The biosynthesis of collagen is increased by approximately 25% by the addition of collagen hydrolysate and only by approximately 5% by the addition of rosehip powder. However, an increase by approximately 50% in relation to the control is observed with the simultaneous addition of collagen hydrolysate and rosehip powder (in a weight ratio of approximately 10:1).

Figure 8:
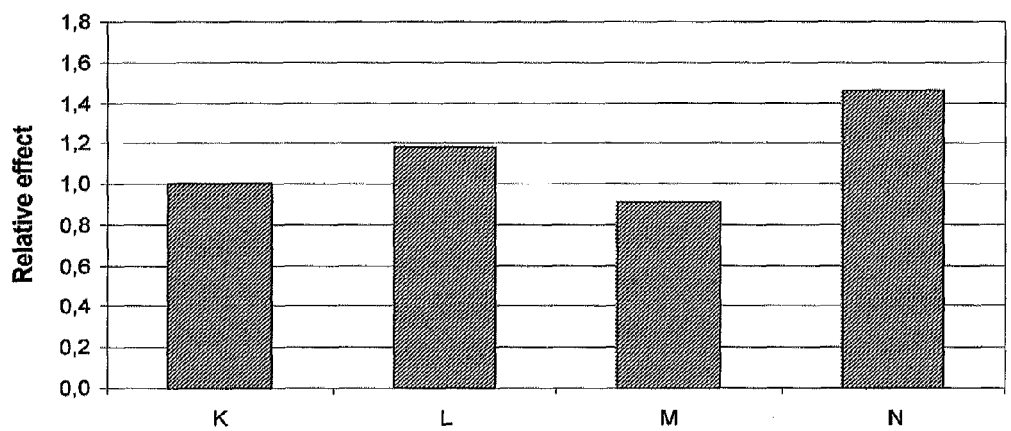
FIG. 8 is a graph relating to the biosynthesis of proteoglycans (rosehip powder)

The values for the biosynthesis of proteoglycans shown in FIG. 8 demonstrate the presence of a synergistic effect even more clearly. The addition of rosehip powder alone (batch M) results in a proteoglycan biosynthesis that is slightly lower than with the control, (batch K), whereas approximately double the increase is achieved as a result of the combination of rosehip powder with collagen hydrolysate (batch N) than as a result of collagen hydrolysate alone (batch L).

Figure 9:
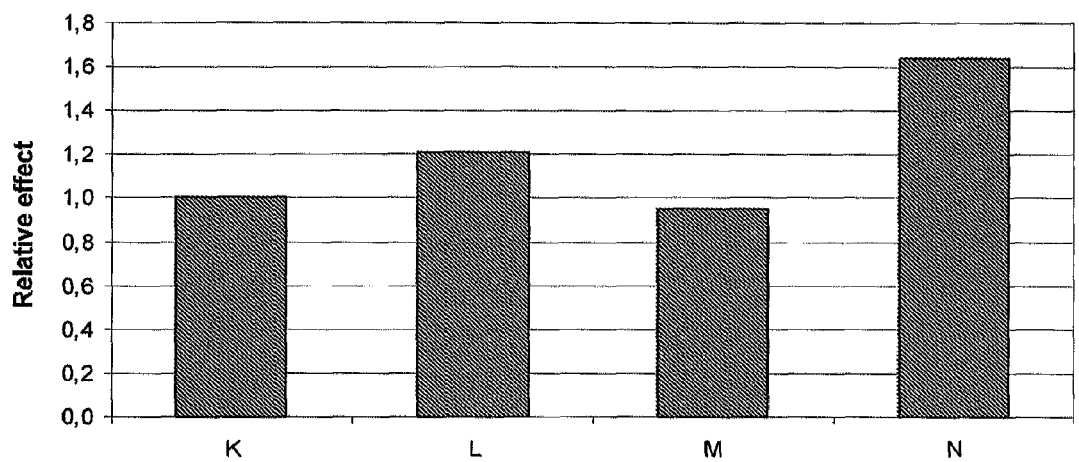
FIG. 9 is a graph relating to the expression of collagen RNA (rosehip powder)
Figure 10:
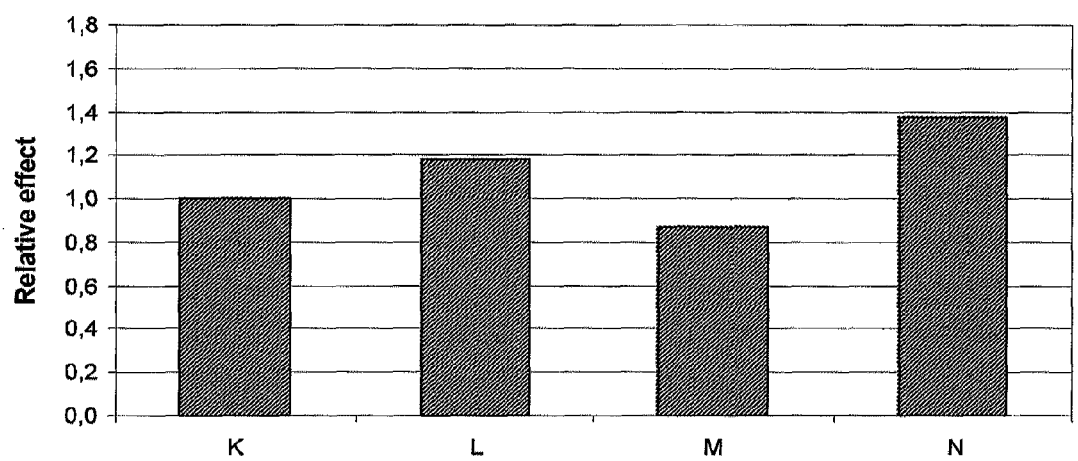
FIG. 10 is a graph relating to the expression of aggrecan RNA (rosehip powder)

The expression of collagen RNA (FIG. 9) and aggrecan RNA (FIG. 10) shows a similar picture. The increase of the expression in relation to the control is about three times higher in the case of batch N or about double (aggrecan RNA) that of batch L.

Figure 11:
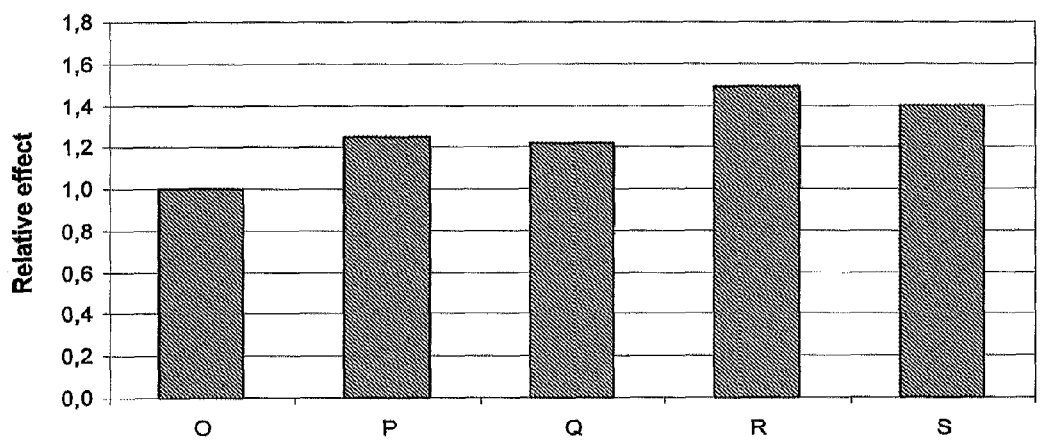
FIG. 11 is a graph relating to the biosynthesis of collagen (rosehip powder)
Figure 12:
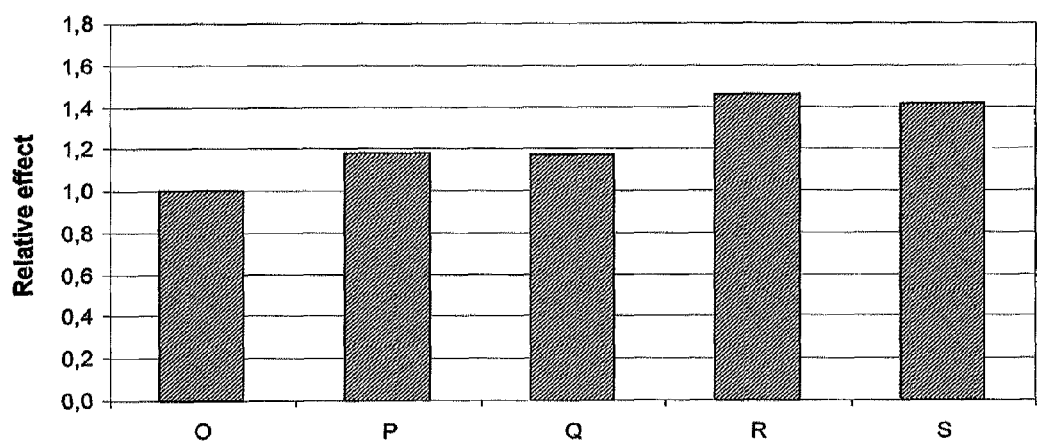
FIG. 12 is a graph relating to the biosynthesis of proteoglycans (rosehip powder).

To determine the effect of the amount of rosehip powder used, a series of tests was conducted with the following batches of cell cultures:

Batch O: control (without collagen hydrolysate or rosehip powder)
Batch P: 0.5 mg/ml of collagen hydrolysate
Batch Q: 0.5 mg/ml of collagen hydrolysate and 0.005 mg/ml of rosehip powder
Batch R: 0.5 mg/ml of collagen hydrolysate and 0.05 mg/ml of rosehip powder
Batch S: 0.5 mg/ml of collagen hydrolysate and 0.5 mg/ml of rosehip powder FIG. 11 shows the results with respect to the biosynthesis of collagen and FIG. 12 with respect to the biosynthesis of proteoglycans. Batch Q (weight ratio of collagen hydrolysate to rosehip powder of 100:1) demonstrates only a slightly higher or lower effect than batch P (only collagen hydrolysate), i.e. an increase in the biosynthesis in the range of approximately 20%. In turn, in the case of batch R (weight ratio of 10:1) a significant increase in the biosynthesis by approximately 50%, corresponding to batch N above, is respectively observed. A further increase in the proportion of rosehip powder to a weight ratio of 1:1 (batch S) leads to a slightly smaller increase than with batch R both in the case of collagen biosynthesis and of proteoglycan biosynthesis.

The above-described results prove that the stimulating effect of collagen hydrolysate on the biosynthesis of the main constituents of the extracellular matrix of the cartilage tissue can be significantly increased by adding rosehip extract or rosehip powder. A composition, which contains collagen hydrolysate and rosehip powder and/or extract in the weight ratio of approximately 2:1 to approximately 100:1, can therefore be used as an effective medication or food supplement for the treatment of degenerative joint diseases.

The invention claimed is:

1. A composition comprising collagen hydrolysate and rosehip powder and/or rosehip extract, wherein the dry mass weight ratio of collagen hydrolysate to rosehip powder and/or extract lies in the range of approximately 10:1 to approximately 20:1.

2. The composition according to claim 1, wherein the collagen hydrolysate is obtained by enzymatic hydrolysis of type I and/or type II collagen.

3. The composition according to claim 1, wherein the collagen hydrolysate has an average molecular weight of approximately 0.3 kDa to approximately 30 kDa.

4. The composition according to claim 1, comprising a rosehip powder composed of *Fructus cynosbati* and/or *Semen cynosbati*.

5. The composition according to claim 4, wherein the rosehip powder is obtained by drying and milling *Fructus cynosbati*.

6. The composition according to claim 1, comprising a rosehip extract composed of *Fructus cynosbati* and/or *Semen cynosbati*.

7. The composition according to claim 6, wherein the rosehip extract is obtained by the extraction of *Fructus cynosbati* with an aqueous extracting agent containing up to 50% by vol. of ethanol.

8. The composition according to claim 7, wherein the rosehip extract is obtained by subsequent enzyme treatment and/or membrane filtration.

9. The composition according to claim 8, wherein the enzyme treatment comprises a treatment of the rosehip extract with one or more enzymes, which are selected from glycosidases, cellulases and pectinases.

10. The composition according to claim 8, wherein the membrane filtration comprises filtration of the rosehip extract with an exclusion size of approximately 1 kDa to approximately 500 kDa.

11. A medication or food supplement comprising the composition according to claim 1.

12. A medication or food supplement according to claim 11 in the form of a solution, a syrup, a powder or a granulate.

13. A medication or food supplement according to claim 11 in the form of tablets, film tablets, capsules, lozenges or sugar-coated pills.

14. A medication or food supplement according to claim 12, wherein a dose of the medication or the food supplement comprises approximately 0.1 g to approximately 20 g of collagen hydrolysate.

15. A method of treating or inhibiting degenerative joint disease comprising orally administering the medication or food supplement according to claim 11 to a subject in need thereof.

16. The method according to claim 15, wherein the joint disease is selected from arthrosis, rheumatoid arthritis, rheumatic-type diseases, spondylitis and fibromyalgia.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: porcine

<400> SEQUENCE: 1
ccactgctct ctgccataca                                            20

<210> SEQ ID NO 2
<211> LENGTH: 20
<212> TYPE: DNA
<213> ORGANISM: porcine

<400> SEQUENCE: 2
gtccaggtag gcaatgctgt                                            20

<210> SEQ ID NO 3
<211> LENGTH: 20
<212> TYPE: DNA
<213> ORGANISM: porcine

<400> SEQUENCE: 3
ggagaagaga tgccaacagc                                            20

<210> SEQ ID NO 4
<211> LENGTH: 20
<212> TYPE: DNA
<213> ORGANISM: porcine

<400> SEQUENCE: 4
atgctgctca ggtgtgactg                                            20

<210> SEQ ID NO 5
<211> LENGTH: 20
<212> TYPE: DNA
<213> ORGANISM: porcine

<400> SEQUENCE: 5
gggcatgaac catgagaagt                                            20

<210> SEQ ID NO 6
<211> LENGTH: 20
```

```
<212> TYPE: DNA
<213> ORGANISM: porcine

<400> SEQUENCE: 6
aagcagggat gatgttctgg                                              20
```